United States Patent [19]

Arnold et al.

[11] 4,162,265

[45] Jul. 24, 1979

[54] AROMATIC ENYNE COMPOUNDS AND THEIR SYNTHESIS

[75] Inventors: Fred E. Arnold, Centerville; Bruce A. Reinhardt, New Carlisle; Frederick L. Hedberg, Xenia, all of Ohio

[73] Assignee: The United States of America as represented by the Secretary of the Air Force, Washington, D.C.

[21] Appl. No.: 946,290

[22] Filed: Sep. 27, 1978

[51] Int. Cl.$^2$ .................... C07C 87/52; C07C 49/76; C07C 39/18

[52] U.S. Cl. .................... 260/578; 260/582; 260/590 D; 528/171; 568/729

[58] Field of Search ............ 260/578, 590 D; 568/729

[56] References Cited

U.S. PATENT DOCUMENTS

| | | | |
|---|---|---|---|
| 2,586,487 | 2/1952 | Schwartzman et al. | 260/578 X |
| 2,852,556 | 9/1958 | Katz et al. | 260/578 X |
| 3,499,763 | 3/1970 | Clecak et al. | 568/729 X |
| 3,624,162 | 11/1971 | Sieber | 568/729 |
| 4,082,806 | 4/1978 | Harris et al. | 260/590 D |
| 4,122,026 | 10/1978 | Osman | 260/578 X |

FOREIGN PATENT DOCUMENTS

1534311 7/1968 France ..................... 568/729

OTHER PUBLICATIONS

Shell Int., "French Patent Abstracts", vol. 6c13, 4:2 (1966).

Wessely et al., "Chem. Ab.", vol. 54, ab. 2229–2230 (1960).

*Primary Examiner*—Winston A. Douglas
*Assistant Examiner*—John Doll
*Attorney, Agent, or Firm*—Joseph E. Rusz; Cedric H. Kuhn

[57] ABSTRACT

Difunctional aromatic enyne compounds are prepared by the catalytic coupling of substituted monoethynyl compounds. The compounds are useful as monomers in polycondensation reactions for the preparation of high molecular weight, thermally stable thermoplastic polymers. On thermal treatment of the polymers, the enyne groups along the polymer backbones react by interchain reactions to provide the solvent and craze resistance required for application as structural materials.

4 Claims, No Drawings

AROMATIC ENYNE COMPOUNDS AND THEIR SYNTHESIS

RIGHTS OF THE GOVERNMENT

The invention described herein may be manufactured and used by or for the Government of the United States for all governmental purposes without the payment of any royalty.

FIELD OF THE INVENTION

This invention relates to aromatic enyne compounds and to a process for their synthesis.

BACKGROUND OF THE INVENTION

In recent years a substantial effort has been devoted to work involving the utilization of thermoplastic resins in fabricating fiber-reinforced composites. Investigations to date have verified that thermoplastic composites and adhesives have the potential of lowering processing costs and increasing the reliability of composite construction. The cost reductions are possible because faster and lower cost manufacturing procedures can be employed. However, because of the problems associated with linear polymeric systems, the use of thermoplastic resins as structural materials in aircraft applications has been limited.

Linear polymers have a very low solvent, creep and craze resistance. Solvents normally found around aircraft and air fields, such as hydraulic fluids, brake fluids, paint strippers, and the like, are potential hazards to such systems. It would, therefore, be highly desirable to have available a thermoplastic material which, when thermally treated, would become lightly crosslinked so as to obviate solvent induced problems inherent in linear polymeric material.

It is a principal object of this invention, therefore, to provide new and improved aromatic monomers which can be used in the preparation of thermally stable, high molecular weight polymers having the ability to react further after fabrication, thereby forming a lightly crosslinked, solvent resistant system.

Another object of the invention is to provide a process for synthesizing the aromatic monomers.

Other objects and advantages of the invention will become apparent to those skilled in the art upon consideration of the accompanying disclosure.

SUMMARY OF THE INVENTION

The present invention resides in difunctional aromatic enyne compounds having the following formula:

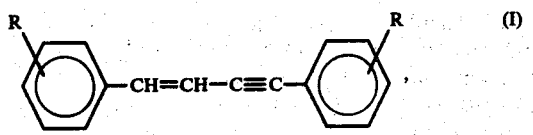

wherein R is a functional group suitable for polycondensation reactions, such as amino (NH$_2$), hydroxyl (OH), and phenoxy benzil

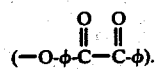

It is to be understood that the symbol $\phi$ represents a phenyl radical.

In one embodiment, the present invention lies in a process for synthesizing aromatic enyne monomers of Formula I in which the R group is amino or hydroxyl. In conducting the process, a three-stage procedure is followed in which the reactions involved are illustrated by the following equations:

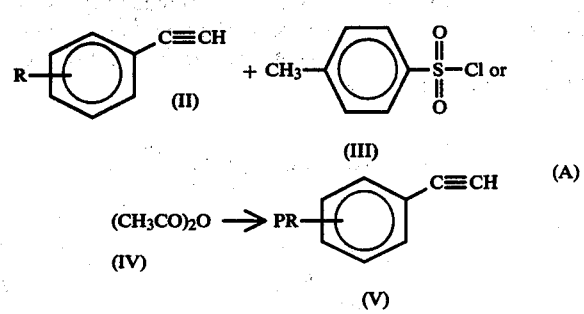

where R equals NH$_2$ or OH and P equals

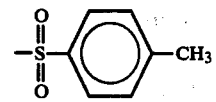

when using compound (III)

when using compound IV.

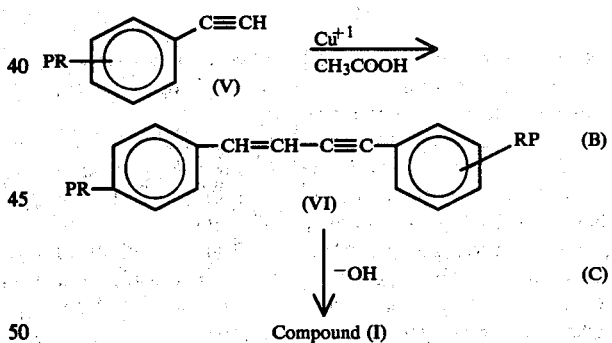

As shown by equation (A), a monofunctional ethynyl compound II in which the R group (NH$_2$ or OH) is meta or para to the ethynyl group is reacted with toluenesulfonyl chloride (III) or acetic anhydride (IV) to form a compound V in which the R group is protected by a tosyl or acetyl group P. The protective group denoted by P can also be described as a toluene sulfonyl or acetyl derivative of the R group. Protection for the R group is required in the subsequent coupling reaction.

According to equation (B), the ethynyl group of compound V is coupled with a copper (cuprous) salt in acetic acid to provide the aromatic enyne structure of compound VI. Suitable cuprous salts include cuprous oxide and cuprous acetate which are used in catalytic amounts. The amount usually ranges from about 0.1 to 30 weight percent, preferably about 10 weight percent, based upon the weight of ethynyl compound V. In the third and final stage of the process (equation C), the enyne aromatic compound VI is hydrolyzed with an inorganic base in an aqueous alcohol medium. Suitable inorganic bases included sodium, potassium or lithium hydroxide. As a result of the hydrolysis reaction, protective group P is removed from compound VI to provide the aromatic enyne monomer I of this invention.

Another embodiment of the invention is concerned with the process for synthesizing the monomer according to Formula I in which R is phenoxy benzil. The reactions involved in the synthesis can be represented by the following equations:

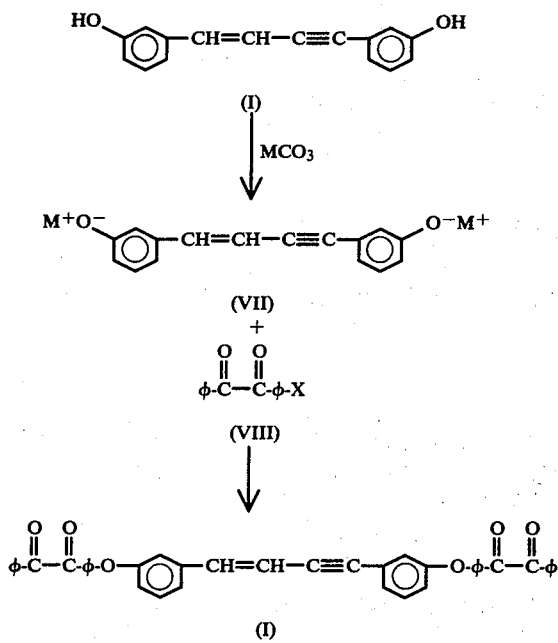

In the foregoing equations, M is an alkali metal, such as potassium or sodium, and X (leaving group) is nitro, fluorine, chlorine, iodine or bromine.

As seen from equation (D), an aromatic enyne compound I of this invention (R=OH) is used as a starting material in synthesizing compound I in which R is a phenoxy benzil group. Initially, a metallic salt (VII) of 1,4-bis(3-hydroxyphenyl)-buta-1-ene-3-yne (compound I wherein R=OH) is generated by reacting compound I (R=OH) with an alkali metal salt, such as potassium carbonate. The enyne dibenzil monomer

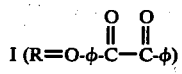

is then prepared (equation E) by the nucleophilic displacement reaction of a nitro or halo leaving group (X) of a benzil VIII with metallic salt VII.

The monomers of this invention as defined by Formula I can be polymerized with conventional comonomers so as to prepare amide, imide, ester, triazine and quinoxaline polymers. For example, imide polymers can be synthesized by the polycondensation of aromatic enyne compound I(R=NH₂) with an aromatic dianhydride such as bis(3,4-dicarboxyphenyl)ether dianhydride or bis(3,4-dicarboxyphenyl)sulfone dianhydride. Also, polyquinoxalines can be prepared by condensing aromatic enyne compound

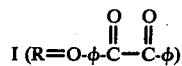

with a bis(o-diamine) such as 3,3'-diaminobenzidine or 3,3',4,4'-tetraaminodiphenylether. The monomers are especially useful in preparing aromatic ethersulfone polymers by the polycondensation of aromatic enyne diol I (R=OH) with dihalodiphenylsulfone as disclosed in commonly assigned, copending U.S. patent application Ser. No. 946,291 filed on Sept. 27, 1978. The disclosure of this copending application is incorporated herein by reference.

When monomers of this invention undergo a condensation reaction with a suitable comonomer, the resulting enyne structure generated along the polymer backbone can further react at higher temperatures. The thermal treatment of such high molecular weight thermoplastic material lightly crosslinks the material by interchain addition reactions. There is thus provided an insoluble system with improved solvent, craze and creep resistance.

A more complete understanding of the invention can be obtained by referring to the following illustrative examples which are not intended, however, to be unduly limitative of the invention.

EXAMPLE I

Preparation of 1,4-Bis(3-aminophenyl)-buta-1-ene-3-yne (R=amino; NH₂)

a. 3-acetamidophenylacetylene.

To a 250 ml 3-neck flask fitted with a condenser, nitrogen inlet and outlet, and magnetic stirrer was added 150 ml of acetic acid and 35 ml of acetic anhydride. The mixture was heated to reflux under nitrogen and cooled under nitrogen. To the cooled mixture was added 15 g (0.114 mole) of 3-aminophenylacetylene and the homogeneous solution was refluxed overnight. The cooled reaction mixture was transferred to a 500 ml one-neck flask, and the acetic acid was removed by a rotor-evaporator under high vacuum. Water (200 ml) was added to the residual oil to crystallize the solid product. The material was isolated by filtration and washed with water and then air dried. Recrystallization from carbon tetrachloride with 200 g/10 g solid plus charcoal yielded 14.4 g (79% yield) of a white crystalline product (m.p. 94°-96° C.).

Analysis Calc'd for $C_{10}H_9NO$: C, 75.47; H, 5.66; N, 8.81; Found: C, 75.12; H, 5.63; N, 8.73.

b. 1,4-Bis-(3-acetamidophenyl)-buta-1-ene-3-yne.

To 350 ml of deoxygenated acetic acid was added 1.4 g of cuprous acetate whereupon a clear blue solution formed. The solution was brought to reflux, under nitrogen, and 14.35 g (0.09 mole) of 3-acetamidophenylacetylene was added as a solid. The reaction mixture was maintained at reflux for 12 hours and cooled to room temperature. Isolation of the material was carried out by precipitation of the reaction mixture into distilled water and collection by filtration. The light tan material was air dried and recrystallized from isopropanol to give 13.8 g of product (96% yield) (m.p. 276°-278° C.).

Analysis Calc'd for $C_{20}H_{18}N_2O_2$: C, 77.89; H, 5.88; N, 9.08; Found: C, 77.35; H, 5.43; N, 8.95.

c. 1,4-Bis-(3-aminophenyl)-buta-1-ene-3-yne.

To 50 ml of a 28% aqueous ethanol solution was added 2.6 g (0.0084 mole) of 1,4-bis-(3-acetamidophenyl)-buta-1-ene-3-yne and the mixture was refluxed for 1 hour. After cooling to room temperature, the reaction mixture was poured into 300 ml of distilled water and extracted with three 100 ml portions of methylene chloride. Removal of the methylene chloride under reduced pressure provided a light yellow material. Recrystallization of the material from a one-to-one mixture of benzene/hexane gave 1 g (50% yield) of product (m.p. 105°–106° C.).

Analysis Calc'd for $C_{16}H_{14}N_2$: C, 82.02; H, 6.02; N, 11.96; Found: C, 81.90; H, 5.97; N, 11.54.

EXAMPLE II

Preparation of
1,4-Bis-(3-hydroxyphenyl)-buta-1-ene-3-yne
(R=hydroxy; OH)

a.
1,4-Bis-[phenyl-(p-toluenesulfonate)]-3-yl-buta-1-ene-3-yne.

To a two liter, 3-necked round bottom flask, equipped with a nitrogen inlet, condenser, and magnetic stirring bar was added 1000 ml glacial acetic acid. The acetic acid was deaerated by bubbling nitrogen through the liquid at reflux for 15 minutes. To the acetic acid at reflux was added 10.60 g (0.0740 mole) of $Cu_2O$ and the resulting suspension was refluxed for 20 minutes. At the end of this period, almost all of the $Cu_2O$ had dissolved and a blue-green solution had developed. To the solution at reflux was then added 100 g (0.368 mole) of 3-ethynyl-p-toluene sulfonate. Upon addition of the tosylate, the solution changed to orange in color. Heating was continued for an additional 1½ hours. The reaction mixture was cooled, filtered, and added dropwise to a stirring suspension consisting of 2500 ml $H_2O$, 300 g $NaHCO_3$, and 200 ml $CH_2Cl_2$. When all the bicarbonate appeared to have reacted, additional solid sodium bicarbonate was added as needed until all the acetic acid reaction mixture had been neutralized. The $CH_2Cl_2$ layer was then separated and the water layer was washed with 100 ml additional $CH_2Cl_2$. The 300 ml $CH_2Cl_2$ layer was washed with two 500 ml portions of $H_2O$, dried with $MgSO_4$ and reduced in volume to approximately 80 ml of a thick viscous oil which was chromatographed on a 60×5 cm dry column (quartz) of silica gel using 2:1 $CH_2Cl_2$-hexane as the eluent. The solvent was evaporated to give 66.0 g (65% yield) of a white crystalline solid (m.p. 138°–139° C.).

Analysis Calc'd for $C_{30}H_{24}O_6S_2$: C, 66.15; H, 4.44; Found: C, 65.83; H, 4.13.

b. 1,4-Bis-(3-hydroxyphenyl)-buta-1-ene-3-yne.

In a 5 liter, 3-necked round bottom flask equipped with a nitrogen inlet and a distillation apparatus was added 125.0 g (0.23 mole) of 1,4-bis-[phenyl-(p-toluene sulfonate)]-3-yl-buta-1-ene-3-yne and 2500 ml of methanol. To the resulting pale yellow suspension was added 51.60 g NaOH in 750 ml of $H_2O$. The reaction mixture was then heated to reflux and approximately 2500 ml of distillate was collected. After the removal of the methanol, 750 ml of water was added and the resulting solution was poured into a mixture of 400 ml of $H_2SO_4$ and 4000 g of ice. The reaction mixture was then stirred until all the ice melted and the resulting precipitate filtered, washed with $H_2O$, air dried for a short time and then dried under high vacuum at room temperature for 24 hours. The solid was recrystallized by stirring in 1000 ml boiling cyclohexane and adding benzene slowly until solution occurred. The purple solution was treated with charcoal, filtered and cooled. The resulting crystals were filtered, air dried for a short time, and dried for 4 hours under high vacuum. A 3.0 g portion of the dried off-white solid was dissolved in 20 ml of 4:1 methylene chloride-acetonitrile and chromatographed on a 60×5 cm dry dolumn (quartz) using 4:1 methylene chloride-acetonitrile as the eluent. The elution was followed by uv light and the large second band was collected. After removal of the solvent under reduced pressure, the resulting white solid (2.3 g) had a melting point of 146°–147° C.

Analysis Calc'd for $C_{16}H_{12}O_2$: C, 81.33, H, 5.12; Found: C, 81.27; H, 4.95.

EXAMPLE III 1,4-Bis-[3-(4-phenylglyoxaloylphenoxy)phenyl]-1-butene-3-yne (R=phenoxy benzil;

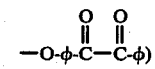

A mixture of 4-nitrobenzil (20.80 g, 0.0816 mole), 1,4-bis(3-hydroxyphenyl)-buta-1-ene-3-yne (7.70 g, 0.0326 mole), potassium carbonate (22.5 g, 0.163 mole) in dimethylsulfoxide (200 ml) was stirred and heated at 60° C. for 20 hours under nitrogen and then poured into 2.5 liters of water. The brownish precipitate was collected, washed with water, dried for 16 hours under vacuum, and extracted thoroughly with boiling carbon tetrachloride. The carbon tetrachloride extracts were chromatographed on silica gel with elution by carbon tetrachloride to remove unreacted 4-nitrobenzil followed by elution with benzene to afford 10.6 g of 1,4-bis[3-(4-phenylglyoxaloylphenoxy)phenyl]-1-butene-3-yne as a yellow oil.

Analysis Calc'd for $C_{44}H_{28}O_6$: C, 84.63; H, 4.52; Found: C, 84.52; H, 4.46.

As seen from the foregoing, the present invention provides difunctional aromatic enyne compounds. Because of their structure, the compounds are useful in polycondensation reactions for preparing high molecular weight, thermally stable thermoplastic polymers. On thermal treatment the enyne groups along the polymer backbones react by interchain reactions to provide the solvent and craze resistance required for application as structural materials.

As will be evident to those skilled in the art, modifications of the present invention can be made in view of the foregoing disclosure without departing from the spirit and scope of the invention.

We claim:

1. A difunctional aromatic enyne compound having the following formula:

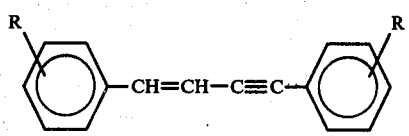

in which R is $NH_2$, OH or 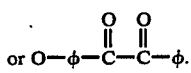
2. The compound according to claim 1 in which R is NH$_2$.
3. The compound according to claim 1 in which R is OH.
4. The compound according to claim 1 in which R is
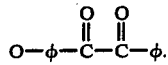
* * * * *